United States Patent
Ergler et al.

(10) Patent No.: US 9,392,985 B2
(45) Date of Patent: Jul. 19, 2016

(54) DIRECT CONVERSION X-RAY DETECTOR

(71) Applicant: Siemens Aktiengesellschaft, Munich (DE)

(72) Inventors: Thorsten Ergler, Forchheim (DE); Andreas Freund, Heroldsbach (DE); Björn Kreisler, Hausen (DJ); Christian Schröter, Bamberg (DE); Stefan Wirth, Erlangen (DE)

(73) Assignee: SIEMENS AKTIENGESELLSCHAFT, Munich (DE)

( * ) Notice: Subject to any disclaimer, the term of this patent is extended or adjusted under 35 U.S.C. 154(b) by 57 days.

(21) Appl. No.: 14/327,630

(22) Filed: Jul. 10, 2014

(65) Prior Publication Data

US 2015/0030120 A1    Jan. 29, 2015

(30) Foreign Application Priority Data

Jul. 26, 2013  (DE) .......................... 10 2013 214 684

(51) Int. Cl.
*A61B 6/00* (2006.01)
*A61B 6/03* (2006.01)
(Continued)

(52) U.S. Cl.
CPC ................ *A61B 6/4208* (2013.01); *A61B 6/032* (2013.01); *A61B 6/06* (2013.01); *A61B 6/4233* (2013.01); *A61B 6/4291* (2013.01); *A61B 6/4488* (2013.01); *G01T 1/244* (2013.01)

(58) Field of Classification Search
CPC ........ A61B 6/032; A61B 6/06; A61B 6/4208; A61B 6/4233; A61B 6/4241; A61B 6/4291; A61B 6/4488; A61B 6/4266; G21K 1/02; G01T 1/20; G01T 1/244; G01N 23/046; G01N 2223/419
See application file for complete search history.

(56) References Cited

U.S. PATENT DOCUMENTS 7,652,258 B2    1/2010  Shahar et al.
2006/0038188 A1*  2/2006  Erchak .................... H01L 33/36
                                                  257/82

(Continued)

FOREIGN PATENT DOCUMENTS

DE          2255465 A1    5/1973
DE     102010015422 A1   10/2011

(Continued)

OTHER PUBLICATIONS

International Search Report PCT/ISA/210 for International Application No. PCT/EP2013/064492 dated Dec. 2, 2013.

(Continued)

*Primary Examiner* — Hoon Song
(74) *Attorney, Agent, or Firm* — Harness, Dickey & Pierce

(57) ABSTRACT

A direct-conversion x-ray detector or x-ray detector module includes: a direct converter; at least one collimator; and at least one radiation source. The at least one collimator is arranged in a direction of radiation of the x-ray radiation in front of the direct converter, and to restrict direct irradiation of the direct converter by the x-ray radiation. The at least one radiation source is at a side of the direct converter, and configured to irradiate the direct converter with additional radiation. The at least one collimator includes: at least one reflection layer on a side facing the direct converter, and configured to reflect the additional radiation onto the direct converter; and a cooling facility configured to cool the at least one radiation source.

20 Claims, 2 Drawing Sheets

(51) Int. Cl.
  *A61B 6/06* (2006.01)
  *G01T 1/24* (2006.01)

(56) References Cited

U.S. PATENT DOCUMENTS

| | | | |
|---|---|---|---|
| 2007/0131867 A1* | 6/2007 | Okada | G01T 1/2018 250/370.09 |
| 2008/0137004 A1* | 6/2008 | Iwasaki | G02B 6/0021 349/64 |
| 2008/0164418 A1* | 7/2008 | Shahar | G01T 1/24 250/370.01 |
| 2010/0086098 A1 | 4/2010 | Shahar et al. | |
| 2011/0253886 A1 | 10/2011 | Hackenschmied et al. | |
| 2015/0221406 A1 | 8/2015 | Dierre et al. | |

FOREIGN PATENT DOCUMENTS

| | | | |
|---|---|---|---|
| DE | 102012200549 B3 | 4/2013 | |
| DE | 102012213409 B3 | 11/2014 | |
| WO | WO-2013120657 A1 | 8/2013 | |
| WO | WO 2014019817 A2 | 2/2014 | |

OTHER PUBLICATIONS

Written Opinion of the International Searching Authority PCT/ISA/237 for International Application No. PCT/EP2013/064492 dated Dec. 2, 2013.

German Examination Report mailed Jun. 25, 2013 for German Application No. 102012213409.3.

Scheubeck M: "Thermische Anforderungen von LED-Leuchten", www.all-electronics.de [online], (Jun. 18, 2012).

German Office Action issued in German Patent Application No. 10 2013 214 684, dated Oct. 28, 2015.

\* cited by examiner

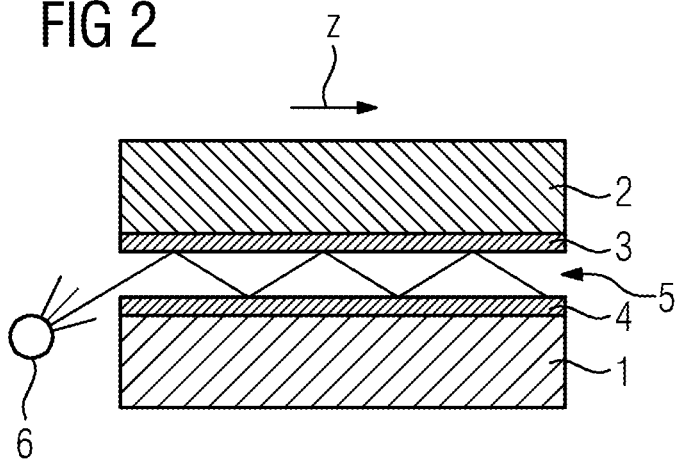
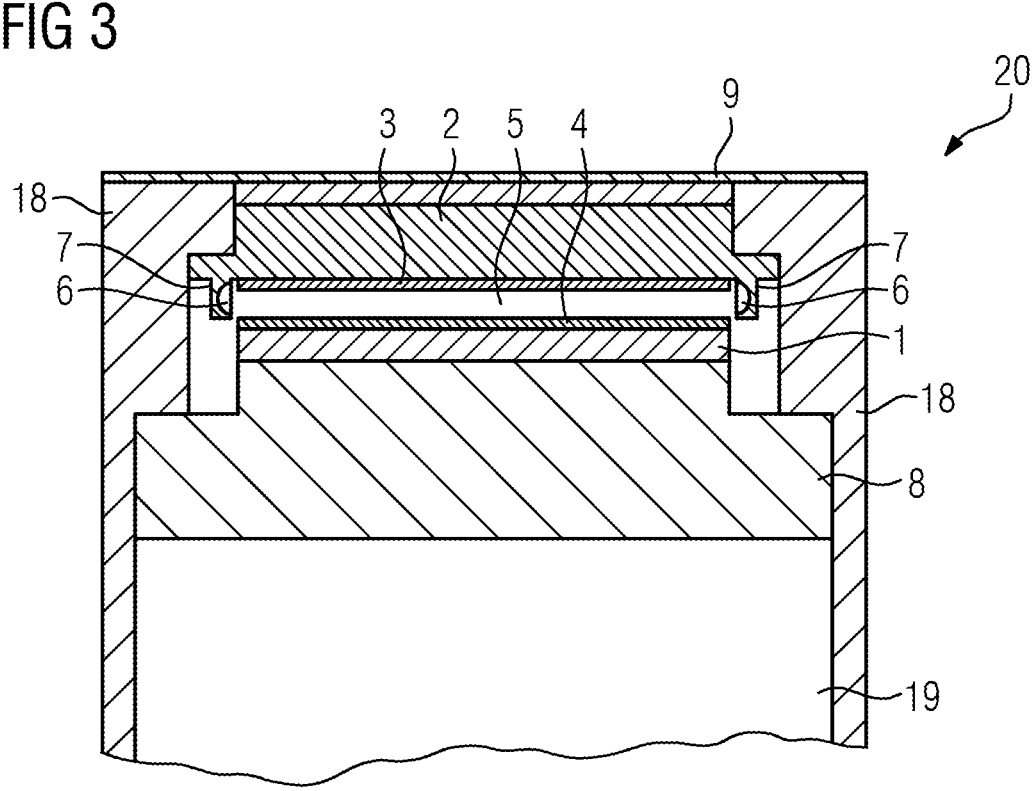

DIRECT CONVERSION X-RAY DETECTOR

PRIORITY STATEMENT

The present application hereby claims priority under 35 U.S.C. §119 to German patent application number DE 102013214684.1 filed Jul. 26, 2013, the entire contents of which are hereby incorporated herein by reference.

FIELD

At least one embodiment of the invention generally relates to a direct-conversion x-ray detector.

BACKGROUND

The detectors used for the detection of Gamma and x-ray radiation, e.g. in CT, Dual-Energy CT, SPECT and PET systems, include direct-conversion radiation detectors, based on semiconductor direct-converter materials, such as CdTe, CdZnTe, CdZnTeSe, CdTeSe, CdMnTe, InP, TlBr2, HgI2. With these materials however, especially with a high radiation flux density necessary for CT devices, the polarization effect occurs.

Polarization refers to the reduction of the detected counting rate at high photon or radiation fluxes. The polarization is caused by the very low mobility of the charge carriers, above all of the electron holes, and through the concentration of intrinsic impurities in the semiconductor. The polarization thus arises through the reduction of the electric field as a result of fixed-location charges bound to the fault points which act as capture and recombination centers for the charge carriers created by the x-ray radiation. This results in a reduction of the charge carrier lifetime and mobility, which in its turn leads to a reduction of the detected count rate at the high radiation flux densities.

The polarization of the semiconducting direct converter material changes during a measurement process. This change of the electric field in its turn results in a change of the measured pulse heights and thus also has an effect on the count rate of the detector, also referred to as drift. Thus the maximum detectable radiation flux of a direct converter is restricted by polarization. Especially with a high radiation flux density necessary for CT devices the polarization effect occurs to an increased extent.

One approach to a solution is to largely anticipate the polarization of the semiconducting direct-conversion material by irradiating the detector with additional x-ray radiation, in that this additional irradiation is carried out directly before a measurement process. This method however is not suitable for operation with patients since the patient would be subjected to an additional dose. Through the additional x-ray irradiation before the measurement process a preloaded state of the detector is set, the semiconducting direct converter material is thus intentionally polarized, so that both calibration actions and also actual measurement processes can be carried out.

In a further approach to a solution the semiconducting direct-converter material is irradiated directly or indirectly with visible radiation, infrared radiation or UV radiation. This irradiation results in a similar conditioning of the detector to its irradiation with x-ray radiation, wherein the IR radiation is easy to handle and is harmless for the patient.

The direct converter can be irradiated directly by the planar cathode for example. Since the direct irradiation path to the direct converter is restricted by the anti-scatter grid and, for an even irradiation, only a narrow gap is present between the lower side of the anti-scatter grid and the upper side of the semiconductor, as described in the subsequently-published patent application with the file reference DE 10 2012 213 409.3 (the entire contents of which are hereby incorporated herein by reference), there can be provision for an indirect irradiation. A reflection layer is disposed on the anti-scatter grid/collimator for this, which reflects an additional radiation evenly onto the direct converter and is illuminated by a radiation source disposed at the side of the direct converter. The relatively high currents which are needed for illumination mean that the radiation source can heat up strongly, which leads, because of its immediate vicinity to the direct converter or to other electronic components of the x-ray detector, to said components heating up and thus to an undesired change in their sensitivity. In addition a heating up of the radiation source leads to the emitted light power changing.

SUMMARY

At least one embodiment of the present invention provides a direct-conversion x-ray detector in which an even irradiation of the direct converter used for detection is possible over a longer period for reduction of polarization and drift.

At least one embodiment of the invention is directed to a direct-conversion x-ray detector. Advantageous embodiments are the subject matter of the dependent claims.

In accordance with at least one embodiment of the invention, a direct-conversion x-ray detector or an x-ray detector module for detection of x-ray radiation is provided, having a direct converter used for detection of the x-ray radiation, at least one collimator disposed in front of the direct converter at least partly in the direction of radiation of the x-ray radiation and at least one radiation source which is disposed to the side of the direct converter and irradiates the direct converter indirectly with an additional radiation, wherein the at least one collimator has at least one reflection layer on a side facing towards the direct converter, on which the additional radiation is reflected onto the direct converter, and having a cooling device, through which the at least on radiation source is able to be cooled. The cooling of the at least one radiation source enables said source to be held at a constant temperature even for a longer period and under variable illumination conditions in a simple manner. This also means that the light power of the at least one radiation source remains constant, which in turn prevents the x-ray detector experiencing a variable heat input, which would influence the sensitivity and cause image artifacts to occur. The cooling thus guarantees a constant reduction of polarization effects and a counting rate drift of the x-ray detector and leads to a higher image quality of x-ray images recorded by way of the x-ray detector.

BRIEF DESCRIPTION OF THE DRAWINGS

The invention and also further advantageous embodiments in accordance with features of the subclaims will be explained below in the drawing in greater detail on the basis of schematic diagrams of example embodiments, without this restricting the invention to the said exemplary embodiments. In the figures:

FIG. 2 shows a sectional diagram of a known x-ray detector with an indirect irradiation source for irradiating a direct converter and FIG. 3 shows a diagram of an embodiment of an inventive x-ray detector.

DETAILED DESCRIPTION OF THE EXAMPLE EMBODIMENTS

Figure 1:
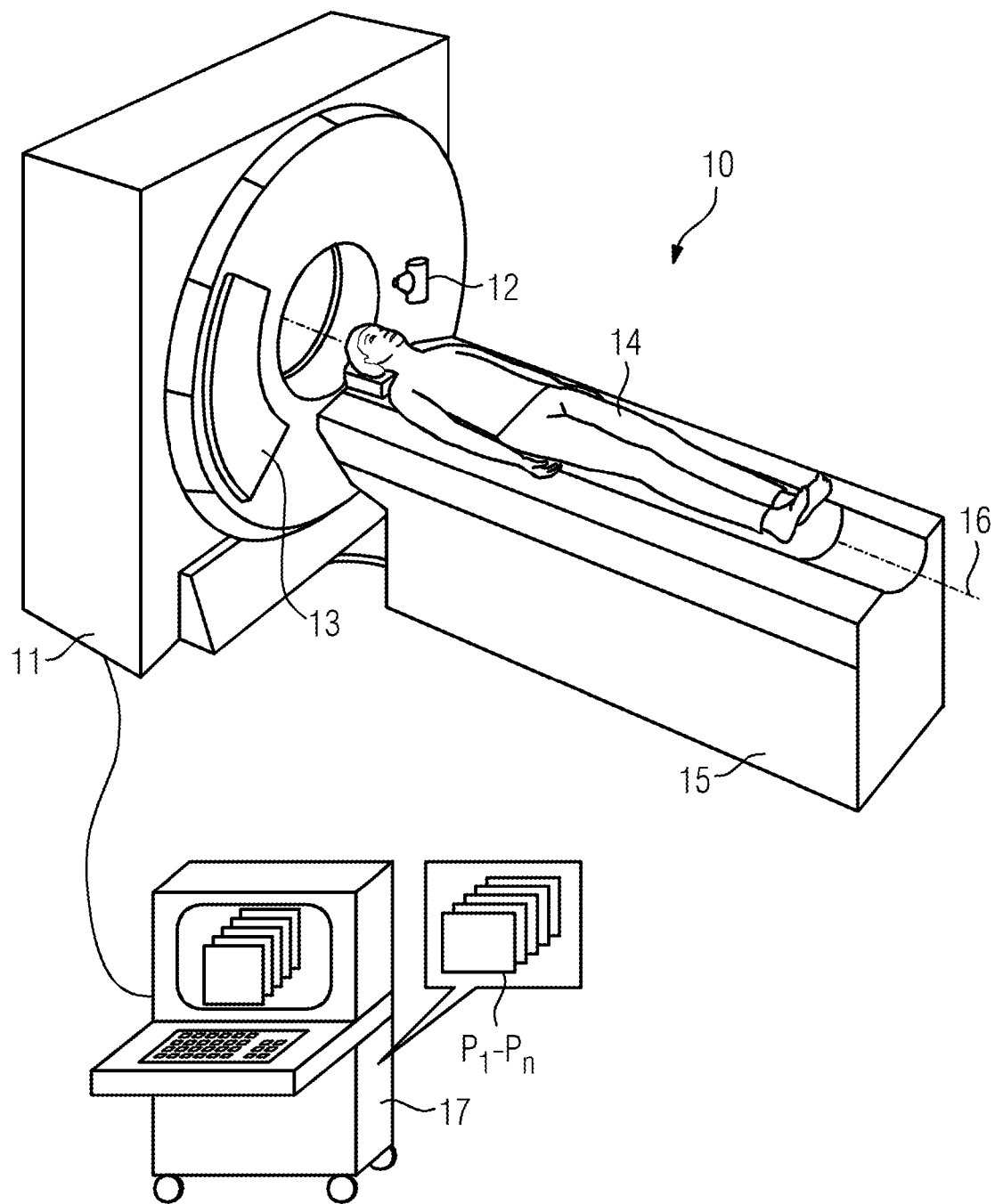
FIG. 1 shows a view of a known computed tomography system with an x-ray detector.

Various example embodiments will now be described more fully with reference to the accompanying drawings in which only some example embodiments are shown. Specific structural and functional details disclosed herein are merely representative for purposes of describing example embodiments. The present invention, however, may be embodied in many alternate forms and should not be construed as limited to only the example embodiments set forth herein.

Accordingly, while example embodiments of the invention are capable of various modifications and alternative forms, embodiments thereof are shown by way of example in the drawings and will herein be described in detail. It should be understood, however, that there is no intent to limit example embodiments of the present invention to the particular forms disclosed. On the contrary, example embodiments are to cover all modifications, equivalents, and alternatives falling within the scope of the invention. Like numbers refer to like elements throughout the description of the figures.

Before discussing example embodiments in more detail, it is noted that some example embodiments are described as processes or methods depicted as flowcharts. Although the flowcharts describe the operations as sequential processes, many of the operations may be performed in parallel, concurrently or simultaneously. In addition, the order of operations may be re-arranged. The processes may be terminated when their operations are completed, but may also have additional steps not included in the figure. The processes may correspond to methods, functions, procedures, subroutines, subprograms, etc.

Methods discussed below, some of which are illustrated by the flow charts, may be implemented by hardware, software, firmware, middleware, microcode, hardware description languages, or any combination thereof. When implemented in software, firmware, middleware or microcode, the program code or code segments to perform the necessary tasks will be stored in a machine or computer readable medium such as a storage medium or non-transitory computer readable medium. A processor(s) will perform the necessary tasks.

Specific structural and functional details disclosed herein are merely representative for purposes of describing example embodiments of the present invention. This invention may, however, be embodied in many alternate forms and should not be construed as limited to only the embodiments set forth herein.

It will be understood that, although the terms first, second, etc. may be used herein to describe various elements, these elements should not be limited by these terms. These terms are only used to distinguish one element from another. For example, a first element could be termed a second element, and, similarly, a second element could be termed a first element, without departing from the scope of example embodiments of the present invention. As used herein, the term "and/or," includes any and all combinations of one or more of the associated listed items.

It will be understood that when an element is referred to as being "connected," or "coupled," to another element, it can be directly connected or coupled to the other element or intervening elements may be present. In contrast, when an element is referred to as being "directly connected," or "directly coupled," to another element, there are no intervening elements present. Other words used to describe the relationship between elements should be interpreted in a like fashion (e.g., "between," versus "directly between," "adjacent," versus "directly adjacent," etc.).

The terminology used herein is for the purpose of describing particular embodiments only and is not intended to be limiting of example embodiments of the invention. As used herein, the singular forms "a," "an," and "the," are intended to include the plural forms as well, unless the context clearly indicates otherwise. As used herein, the terms "and/or" and "at least one of" include any and all combinations of one or more of the associated listed items. It will be further understood that the terms "comprises," "comprising," "includes," and/or "including," when used herein, specify the presence of stated features, integers, steps, operations, elements, and/or components, but do not preclude the presence or addition of one or more other features, integers, steps, operations, elements, components, and/or groups thereof.

It should also be noted that in some alternative implementations, the functions/acts noted may occur out of the order noted in the figures. For example, two figures shown in succession may in fact be executed substantially concurrently or may sometimes be executed in the reverse order, depending upon the functionality/acts involved.

Unless otherwise defined, all terms (including technical and scientific terms) used herein have the same meaning as commonly understood by one of ordinary skill in the art to which example embodiments belong. It will be further understood that terms, e.g., those defined in commonly used dictionaries, should be interpreted as having a meaning that is consistent with their meaning in the context of the relevant art and will not be interpreted in an idealized or overly formal sense unless expressly so defined herein.

Portions of the example embodiments and corresponding detailed description may be presented in terms of software, or algorithms and symbolic representations of operation on data bits within a computer memory. These descriptions and representations are the ones by which those of ordinary skill in the art effectively convey the substance of their work to others of ordinary skill in the art. An algorithm, as the term is used here, and as it is used generally, is conceived to be a self-consistent sequence of steps leading to a desired result. The steps are those requiring physical manipulations of physical quantities. Usually, though not necessarily, these quantities take the form of optical, electrical, or magnetic signals capable of being stored, transferred, combined, compared, and otherwise manipulated. It has proven convenient at times, principally for reasons of common usage, to refer to these signals as bits, values, elements, symbols, characters, terms, numbers, or the like.

In the following description, illustrative embodiments may be described with reference to acts and symbolic representations of operations (e.g., in the form of flowcharts) that may be implemented as program modules or functional processes include routines, programs, objects, components, data structures, etc., that perform particular tasks or implement particular abstract data types and may be implemented using existing hardware at existing network elements. Such existing hardware may include one or more Central Processing Units (CPUs), digital signal processors (DSPs), application-specific-integrated-circuits, field programmable gate arrays (FPGAs) computers or the like.

Note also that the software implemented aspects of the example embodiments may be typically encoded on some form of program storage medium or implemented over some type of transmission medium. The program storage medium (e.g., non-transitory storage medium) may be magnetic (e.g., a floppy disk or a hard drive) or optical (e.g., a compact disk read only memory, or "CD ROM"), and may be read only or random access. Similarly, the transmission medium may be twisted wire pairs, coaxial cable, optical fiber, or some other suitable transmission medium known to the art. The example embodiments not limited by these aspects of any given implementation.

It should be borne in mind, however, that all of these and similar terms are to be associated with the appropriate physical quantities and are merely convenient labels applied to these quantities. Unless specifically stated otherwise, or as is apparent from the discussion, terms such as "processing" or "computing" or "calculating" or "determining" of "displaying" or the like, refer to the action and processes of a computer system, or similar electronic computing device/hardware, that manipulates and transforms data represented as physical, electronic quantities within the computer system's registers and memories into other data similarly represented as physical quantities within the computer system memories or registers or other such information storage, transmission or display devices.

Spatially relative terms, such as "beneath", "below", "lower", "above", "upper", and the like, may be used herein for ease of description to describe one element or feature's relationship to another element(s) or feature(s) as illustrated in the figures. It will be understood that the spatially relative terms are intended to encompass different orientations of the device in use or operation in addition to the orientation depicted in the figures. For example, if the device in the figures is turned over, elements described as "below" or "beneath" other elements or features would then be oriented "above" the other elements or features. Thus, term such as "below" can encompass both an orientation of above and below. The device may be otherwise oriented (rotated 90 degrees or at other orientations) and the spatially relative descriptors used herein are interpreted accordingly.

Although the terms first, second, etc. may be used herein to describe various elements, components, regions, layers and/or sections, it should be understood that these elements, components, regions, layers and/or sections should not be limited by these terms. These terms are used only to distinguish one element, component, region, layer, or section from another region, layer, or section. Thus, a first element, component, region, layer, or section discussed below could be termed a second element, component, region, layer, or section without departing from the teachings of the present invention.

In accordance with at least one embodiment of the invention, a direct-conversion x-ray detector or an x-ray detector module for detection of x-ray radiation is provided, having a direct converter used for detection of the x-ray radiation, at least one collimator disposed in front of the direct converter at least partly in the direction of radiation of the x-ray radiation and at least one radiation source which is disposed to the side of the direct converter and irradiates the direct converter indirectly with an additional radiation, wherein the at least one collimator has at least one reflection layer on a side facing towards the direct converter, on which the additional radiation is reflected onto the direct converter, and having a cooling device, through which the at least on radiation source is able to be cooled. The cooling of the at least one radiation source enables said source to be held at a constant temperature even for a longer period and under variable illumination conditions in a simple manner. This also means that the light power of the at least one radiation source remains constant, which in turn prevents the x-ray detector experiencing a variable heat input, which would influence the sensitivity and cause image artifacts to occur. The cooling thus guarantees a constant reduction of polarization effects and a counting rate drift of the x-ray detector and leads to a higher image quality of x-ray images recorded by way of the x-ray detector.

In particular, there is a gap between the direct converter and the at least one collimator for the additional radiation. The indirect irradiation and reflection of the radiation on the reflection layer enables the direct converter to be irradiated evenly and over a large surface area. An arrangement of the radiation source to the side is to be understood as the said source being disposed outside the gap and outside the usual beam path of the x-ray radiation, essentially next to the direct converter or next to the gap.

Reflector lacquers having a high reflectivity and insensitivity to x-ray radiation are suitable as reflective materials. Materials such as metals, especially light metals in the form of metallic films or metal films applied by vapor deposition, plastics, especially layered plastics, compounds such as metal alloys or semiconductors, are also suitable as materials.

In order to guarantee an especially even irradiation, two radiation sources are disposed on two sides of the direct converter.

In accordance with an embodiment of the invention, the collimator is embodied at least partly from a thermally-conductive material and the at least one radiation source is integrated into at least one heat sink which is in thermal contact with the collimator. In accordance with a further embodiment of the invention the heat sink is additionally an integral component of the collimator. Through a direct or indirect coupling of the cooling of the radiation source to the collimator a sufficiently large heat sink, including the collimator, is available to guarantee a constant cooling of the radiation source or radiation sources. By using the collimator as a heat sink barely any additional constructional outlay is necessary and the cooling can be provided in a simple and inexpensive manner.

In an advantageous way, for an especially good cooling effect, the collimator is formed from metal and has either metal ribs or metal gratings. Such a mechanical embodiment of the collimator means that said collimator is especially effective as a heat sink.

In accordance with a further embodiment of the invention, the at least one radiation source is embodied as one or more light emitting diodes (LEDs). Light emitting diodes are especially small and powerful, energy-saving and generate relatively little waste heat.

In accordance with a further embodiment of the invention, the radiation source is embodied for emitting infrared radiation. Other types of radiation, e.g. visible light or UV light, can also be used.

The x-ray detector is especially embodied as a computed tomography x-ray detector for use in CT system. The necessary high radiation flux density in computed tomography means that an inventive x-ray detector has an especially great benefit here. The x-ray detector can however also be used in other areas, e.g. angiography, and embodied as a flat panel detector for example.

FIG. 1 shows an example of the computed tomography (CT) system 10. The CT system 10 comprises a gantry housing 11, in which a gantry not shown in any greater detail here is located, to which an x-ray tube 12 with an x-ray detector 13 lying opposite it is attached. (Optionally a second x-ray tube with a second opposing x-ray detector can be provided). A patient 14 is located on a patient couch 15 able to be moved in the direction of the system axis 16, with which he or she can be pushed during the scanning with the x-ray radiation continually or sequentially along the system axis 16 or in the z direction through a measurement field between the x-ray tube 12 and the assigned x-ray detector 13. This process is controlled by a processing and control unit 17 with the aid of computer programs P1 to Pn.

The x-ray detector 13 is embodied here, in the embodiment of the CT system 10 shown by way of example, as a direct-conversion x-ray detector, having at least one direct converter in the form of a semiconductor material used for detection of the x-ray radiation, a collimator and a radiation source disposed to the side, which irradiates the direct converter with an additional radiation. X-ray detectors suitable for computed tomography are frequently embodied as line detectors, in which many pixel elements are disposed as long lines but only a few (e.g. two) lines are present in total.

FIG. 2 shows a schematic diagram of a direct converter 1 of an x-ray detector or an x-ray detector module (if an x-ray detector is constructed from a number of modules for example) used for detection of x-ray radiation, e.g. in a CT system (FIG. 1). The material of the direct converter 1 is generally a semiconductor material, for example CdTe or CZT. Also shown is a collimator 2, which is disposed at a distance from and in parallel with the direct converter 1. A gap 5 is embodied between the direct converter 1 and the collimator 2. The direct converter 1, on its surface lying opposite the collimator 2, has an electrode 4 which has a specific transmission level.

The electrode 4 is connected for example to the electronics of the CT system, which is not shown in the diagram however for reasons of clarity. Disposed on a front side of the direct converter 1, viewed in the z direction, is a radiation source 6 in the form of a light emitting diode or an LED array outside the gap 5. The light emitting diode or the LED array emit radiation in the Z direction into the gap 5. The radiation involved is infrared radiation for example. Embodied on the surface opposite the direct converter 1, i.e. the underside of the collimator 2, is a reflection layer 3. Through the relatively high currents which are needed for illumination, the LED or the LED array can heat up strongly, which leads, through its direct proximity to the x-ray detector, to the latter heating up and thus to an undesired change in its sensitivity. In addition a heating up of the LED (array) leads to the emitted light power changing.

FIG. 3 shows an x-ray detector module 20 (an x-ray detector can be constructed from one or more such x-ray detector modules), in which a cooling facility for cooling two radiation sources 6 is provided and is disposed on the x-ray detector module. The x-ray detector module 20 has a direct converter 1 (e.g. a semiconductor material, for example CdTe or CZT), a collimator 2, a reflection layer 3, an electrode 4 and an air gap 5, as already shown in FIG. 2. The direct converter 1 is disposed on a module carrier 8 and disposed in the direction of radiation below the module carrier in its turn is a module backplane 19. Provided in the direction of radiation above the collimator 2 is an entry aperture 9; in addition the layer structure is surrounded by a detector mechanism 18. The radiation sources 6 are disposed for example on one, two, three or four sides (for a planar embodiment of the x-ray detector module) of the gap 5 in the immediate vicinity of the direct converter 1. The radiation sources irradiate the direct converter for example by means of infrared light (or another radiation frequency). As described, this is done by means of indirect irradiation by means of reflection. The radiation sources 6 are embodied for example as LEDs or LED arrays. Just one radiation source or a plurality of radiation sources can also be provided. In order to avoid a heating up of the radiation sources 6, heat sinks 7 are arranged such that the radiation sources are in contact with the heat sinks for exchange of heat or are integrated partly or completely for cooling into the heat sinks. The heat sinks are embodied from a thermally-conductive material, e.g. from metal.

The heat sink 7 can, as is shown in FIG. 3, be embodied and disposed for example such that it is an integral component of the collimator. In such a case, as shown, the collimator is embodied from a thermally-conductive material; thus it can be embodied for example as a one- or two-dimensional metal grid (ribs or gratings). A part of the collimator then extends as a heat sink around the radiation sources 6 i.e. to the side of the gap 5 for example. As an alternative there are can also be provision for the radiation sources to be integrated into heat sinks (e.g. independent metal blocks) and for the heat sinks to be connected conductively to the collimator made from thermally-conductive material.

The cooling through direct or indirect coupling to the collimator enables the radiation sources to be kept at a constant temperature even under variable illumination conditions. This means that on the one hand the sensitivity of the x-ray detector module remains constant, so that a reliable high-quality x-ray imaging can be carried out. On the other hand the cooling enables the radiation sources (e.g. LEDs/LED arrays) to have a constant light power.

Where the heat sink is integrated into the collimator, receptacles for the radiation sources can already be provided during the manufacturing of the collimator, by which additional components or manufacturing steps (thermally-conductive gluing of the heat sinks to the collimator) can be avoided.

The x-ray detector module depicted in FIG. 3 can be embodied as one x-ray detector (i.e. single) or a plurality of such x-ray detector modules can be provided, which form one larger x-ray detector. At least one embodiment, the inventive x-ray detector can be provided as a line detector, e.g. for computed tomography, or as a flat panel detector, e.g. for angiography or mammography.

At least one embodiment of the invention can be briefly summarized as follows: A direct-conversion x-ray detector or x-ray detector module for detection of x-ray radiation is provided for especially high-quality x-ray imaging, having a direct converter for detection of the x-ray radiation, at least one collimator disposed at least partly in the direction of radiation of the x-ray radiation in front of the direct converter and at least one radiation source which is disposed to the side of the direct converter and irradiates the direct converter indirectly with an additional radiation, wherein the at least one collimator, on a side facing towards the direct converter, has a least one reflection layer, on which the additional radiation is reflected onto the direct converter, and having a cooling facility, through which the at least one radiation source is able to be cooled.

The patent claims filed with the application are formulation proposals without prejudice for obtaining more extensive patent protection. The applicant reserves the right to claim even further combinations of features previously disclosed only in the description and/or drawings.

The example embodiment or each example embodiment should not be understood as a restriction of the invention. Rather, numerous variations and modifications are possible in the context of the present disclosure, in particular those variants and combinations which can be inferred by the person skilled in the art with regard to achieving the object for example by combination or modification of individual features or elements or method steps that are described in connection with the general or specific part of the description and are contained in the claims and/or the drawings, and, by way of combinable features, lead to a new subject matter or to new method steps or sequences of method steps, including insofar as they concern production, testing and operating methods.

References back that are used in dependent claims indicate the further embodiment of the subject matter of the main claim by way of the features of the respective dependent claim; they should not be understood as dispensing with obtaining independent protection of the subject matter for the combinations of features in the referred-back dependent claims. Furthermore, with regard to interpreting the claims, where a feature is concretized in more specific detail in a subordinate claim, it should be assumed that such a restriction is not present in the respective preceding claims.

Since the subject matter of the dependent claims in relation to the prior art on the priority date may form separate and independent inventions, the applicant reserves the right to make them the subject matter of independent claims or divisional declarations. They may furthermore also contain independent inventions which have a configuration that is independent of the subject matters of the preceding dependent claims.

Further, elements and/or features of different example embodiments may be combined with each other and/or substituted for each other within the scope of this disclosure and appended claims.

Still further, any one of the above-described and other example features of the present invention may be embodied in the form of an apparatus, method, system, computer program, tangible computer readable medium and tangible computer program product. For example, of the aforementioned methods may be embodied in the form of a system or device, including, but not limited to, any of the structure for performing the methodology illustrated in the drawings.

Even further, any of the aforementioned methods may be embodied in the form of a program. The program may be stored on a tangible computer readable medium and is adapted to perform any one of the aforementioned methods when run on a computer device (a device including a processor). Thus, the tangible storage medium or tangible computer readable medium, is adapted to store information and is adapted to interact with a data processing facility or computer device to execute the program of any of the above mentioned embodiments and/or to perform the method of any of the above mentioned embodiments.

The tangible computer readable medium or tangible storage medium may be a built-in medium installed inside a computer device main body or a removable tangible medium arranged so that it can be separated from the computer device main body. Examples of the built-in tangible medium include, but are not limited to, rewriteable non-volatile memories, such as ROMs and flash memories, and hard disks. Examples of the removable tangible medium include, but are not limited to, optical storage media such as CD-ROMs and DVDs; magneto-optical storage media, such as MOs; magnetism storage media, including but not limited to floppy disks (trademark), cassette tapes, and removable hard disks; media with a built-in rewriteable non-volatile memory, including but not limited to memory cards; and media with a built-in ROM, including but not limited to ROM cassettes; etc. Furthermore, various information regarding stored images, for example, property information, may be stored in any other form, or it may be provided in other ways.

Although the invention has been illustrated and described in greater detail by the preferred example embodiment, the invention is not restricted by the disclosed examples and other variations can be derived therefrom by the person skilled in the art, without departing from the scope of protection of the invention.

What is claimed is:

1. A direct-conversion x-ray detector or x-ray detector module for detection of x-ray radiation, comprising:
   a direct converter to detect x-ray radiation;
   at least one collimator arranged in front of the direct converter in a direction of radiation of the x-ray radiation, the at least one collimator configured to restrict direct irradiation of the direct converter by the x-ray radiation; and
   at least one radiation source at a side of the direct converter, the at least one radiation source configured to irradiate the direct converter with additional radiation;
   wherein the at least one collimator includes
      at least one reflection layer on a side facing the direct converter, the at least one reflection layer configured to reflect the additional radiation onto the direct converter, and
      a cooling facility configured to cool the at least one radiation source; and
   wherein the additional radiation is one of visible and infrared radiation.

2. The x-ray detector of claim 1, wherein
   the at least one collimator is at least partly formed of a thermally-conductive material; and
   the at least one radiation source is integrated into at least one heat sink, which is thermally-conductively connected to the at least one collimator.

3. The x-ray detector of claim 1, wherein
   the at least one collimator is at least partly formed of a thermally-conductive material; and
   the at least one radiation source is integrated into at least one heat sink, which is an integral component of the at least one collimator.

4. The x-ray detector of claim 1, wherein the at least one collimator is composed of metal and includes one of metal ribs and metal gratings.

5. The x-ray detector of claim 1, wherein the at least one radiation source includes one or more light-emitting diodes (LEDs).

6. The x-ray detector of claim 1, wherein the at least one radiation source is configured to emit infrared radiation.

7. The x-ray detector of claim 1, wherein the at least one radiation source includes two radiation sources, the two radiation sources arranged on at least two sides of the direct converter.

8. The x-ray detector of claim 1, wherein the direct converter and the at least one collimator are separated by a gap for the additional radiation.

9. The x-ray detector of claim 1, wherein the x-ray detector is a computed tomography x-ray detector for use in a computed tomography (CT) system.

10. The x-ray detector of claim 2, wherein the at least one collimator is composed of metal and includes one of metal ribs and metal gratings.

11. The x-ray detector of claim 3, wherein the at least one collimator is composed of metal and includes one of metal ribs and metal gratings.

12. The x-ray detector of claim 2, wherein the at least one radiation source includes one or more light-emitting diodes (LEDs).

13. The x-ray detector of claim 2, wherein the at least one radiation source is configured to emit infrared radiation.

14. The x-ray detector of claim 5, wherein the at least one radiation source is configured to emit infrared radiation.

15. The x-ray detector of claim 5, wherein the at least one radiation source includes two radiation sources, the two radiation sources arranged on at least two sides of the direct converter.

16. The x-ray detector of claim 6, wherein the at least one radiation source includes two radiation sources, the at least two radiation sources arranged on at least two sides of the direct converter.

17. The x-ray detector of claim 3, wherein the at least one collimator is composed of metal and includes one of metal ribs and metal gratings.

18. The x-ray detector of claim 3, wherein the at least one radiation source includes one or more light-emitting diodes (LEDs).

19. A computed tomography (CT) system comprising:
   the x-ray detector of claim 2, wherein the x-ray detector is a CT x-ray detector.

20. A computed tomography (CT) system comprising:
   the x-ray detector of claim 3, wherein the x-ray detector is a CT x-ray detector.

\* \* \* \* \*